(12) United States Patent
Cooper et al.

(10) Patent No.: US 7,214,505 B1
(45) Date of Patent: May 8, 2007

(54) CELL-BASED ASSAY FOR THE DETECTION OF TOXIC ANALYTES

(75) Inventors: Colin Cooper, Shardlow (GB); Edman Tsang, Reading (GB); Robbie Burch, Belfast (GB); Jay Lewington, Woking (GB)

(73) Assignee: Strategic Diagnostics Inc., Newark, DE (US)

( * ) Notice: Subject to any disclaimer, the term of this patent is extended or adjusted under 35 U.S.C. 154(b) by 0 days.

(21) Appl. No.: 09/979,699

(22) PCT Filed: May 5, 2000

(86) PCT No.: PCT/US00/12503

§ 371 (c)(1),
(2), (4) Date: Mar. 19, 2003

(87) PCT Pub. No.: WO00/68367

PCT Pub. Date: Nov. 16, 2000

(30) Foreign Application Priority Data

May 6, 1999 (GB) .................................. 9910499.4

(51) Int. Cl.
*C12Q 1/02* (2006.01)
(52) U.S. Cl. ........................................ 435/29; 435/909
(58) Field of Classification Search ................ 435/29, 435/8, 252.3, 909; 436/172
See application file for complete search history.

(56) References Cited

U.S. PATENT DOCUMENTS

| | | | |
|---|---|---|---|
| 4,581,335 A | 4/1986 | Baldwin | |
| 4,956,295 A * | 9/1990 | Sudoma | 435/252.1 |
| 5,441,873 A | 8/1995 | Knight et al. | |
| 5,739,004 A * | 4/1998 | Woodson | 435/31 |
| 5,827,678 A * | 10/1998 | Hesslewood et al. | 435/29 |
| 5,919,645 A | 7/1999 | Tung et al. | |
| 6,340,572 B1 * | 1/2002 | Becvar et al. | 435/8 |
| 6,475,719 B1 * | 11/2002 | Karp et al. | 435/6 |
| 6,855,513 B1 * | 2/2005 | Whiteley et al. | 435/34 |
| 2002/0028445 A1 | 3/2002 | Bercher | |

FOREIGN PATENT DOCUMENTS

| | | |
|---|---|---|
| DE | 3833628 A1 | 3/1988 |
| JP | 63294785 | 1/1988 |
| WO | WO 87/02704 | 5/1987 |
| WO | WO 95/10767 * | 4/1995 |
| WO | WO 99/09201 | 2/1999 |

OTHER PUBLICATIONS

Fava F. et al. Aerobic Dechlorination of Low Chlorinated Biphenyls by Bacterial Biofilms in Packed Bed Batch Bioreactors. Applied Microbiology Biotechnology 1996 45(4):562-568.*

* cited by examiner

*Primary Examiner*—Ralph Gitomer
(74) *Attorney, Agent, or Firm*—Kilpatrick Stockton LLP

(57) ABSTRACT

Cell-based reagents and methods of using the reagents for detecting analytes are provided. The adsorbing of cells with signal-generating metabolic activity to solid supports has been found to improve the sensitivity of known cell based assays. Signal-generating cells adsorbed to a solid support are introduced to a test agent, and the measured decrease in metabolic signal provides a measure of the toxicity of the test agent.

14 Claims, 5 Drawing Sheets

CELL-BASED ASSAY FOR THE DETECTION OF TOXIC ANALYTES

CROSS REFERENCE TO RELATED APPLICATIONS

This application is the national phase of International Application No. PCT/US00/12503 filed May 5, 2000, which claims priority to GB 9910499.4, filed May 6, 1999, the contents of which are hereby incorporated by reference.

The present invention is concerned with a cell-derived assay reagent and, in particular, with assays for identifying toxic analytes.

BACKGROUND OF THE INVENTION

The use of bacteria with a signal-generating metabolic activity as indicators of toxicity is well established. UK patent number GB 2005018 describes a method of assaying a liquid sample for toxic substances which involves contacting a suspension of bioluminescent microorganisms with a sample suspected of containing a toxic substance and observing the change in the light output of the bioluminescent organisms as a result of contact with the suspected toxic substance. Furthermore, a toxicity monitoring system embodying the same assay principle, which is manufactured and sold under the trademark Microtox®, is in routine use in both environmental laboratories and for a variety of industrial applications. A toxicity assay using bioluminescent bacteria which have been killed, as by radiation, is described in International Patent Application Number WO 95/10767.

Although the methods and reagents utilized previously in systems such as the aforementioned Microtox® system are sensitive and reliable indicators of the presence of toxic substances, there still exists a need to provide reagents and assays having even greater sensitivity than those used heretofore.

SUMMARY OF THE INVENTION

Therefore, it is an object of the present invention to provide novel assay reagents and methods of using such reagents which improve the sensitivity of existing assays for identifying toxic substances.

According to a first aspect of the invention, there is provided a method of assaying a toxic analyte comprising the steps of a) contacting an analyte to be assayed with a preparation of eukaryotic or prokaryotic cells having signal-generating metabolic activity, wherein either said analyte or said preparation has been adsorbed onto a solid phase carrier (b) measuring the level of signal generated in step (a) compared to the signal generated by contacting said analyte and said preparation neither of which have been so adsorbed onto a solid carrier, and (c) using the measurement obtained in (b) as an indicator of the toxicity of said analyte.

As illustrated in more detail in the examples provided below and the accompanying Figures, immobilization or adsorption of the cellular preparation or the analyte advantageously provides an enhanced signal-generating response upon exposure to toxic chemicals. Contact with toxic materials adversely affects the metabolism of eukaryotic or prokaryotic cells, resulting in a corresponding reduction in signal output, which reduction is enhanced due to the adsorption upon the solid carrier. The immobilized preparation of cells or said adsorbed analyte embodies features of the invention.

In a further aspect, the invention provides a method of preparing an assay reagent for assaying a potentially toxic analyte comprising the steps of immobilizing or adsorbing onto a solid-phase carrier one of a preparation of eukaryotic or prokaryotic cells having signal-generating metabolic activity or an analyte to be assayed. The preparation preferably comprises bacterial cells and more preferably bacterial cells which exhibit bioluminescence. The carrier is preferably particulate and may be an inorganic material such as silica or alumina or an organic material having appropriate adsorbent characteristics.

In a preferred embodiment, a preparation of eukaryotic or prokaryotic cells is immobilized onto the carrier, and as illustrated in the following examples, immobilization of the cells results in their increased sensitivity to the toxic substance.

Once a preparation of cells is immobilized or adsorbed upon an appropriate particulate solid carrier for use as an assay reagent, it is preferably stabilized for ease of storage or shipment or the like. Cells can be stabilized using techniques known to those of skill in the art, such as freeze-drying (lyophilization) or other cell preservation techniques known in the art. Prior to contacting the cells with the analyte of interest, the cells on the solid substrate are preferably reconstituted, as by mixing with a reconstitution buffer to provide desired concentration of cells, and then contacted with the analyte. It is further preferable that the stabilized assay reagent be reconstituted immediately prior to use, however allowing the reagent sufficient time to reach a stable, high level of signal-generating activity.

In a still further aspect, an assay kit is provided suitable for performing such an assay comprising an assay reagent, as defined herein, and means for contacting such assay reagent with an analyte to be assayed.

BRIEF DESCRIPTION OF THE FIGURES

The present invention may be more clearly understood by way of the following examples with reference to the accompanying Figures wherein.

DETAILED DESCRIPTION OF THE PREFERRED EMBODIMENTS

Figure 1:
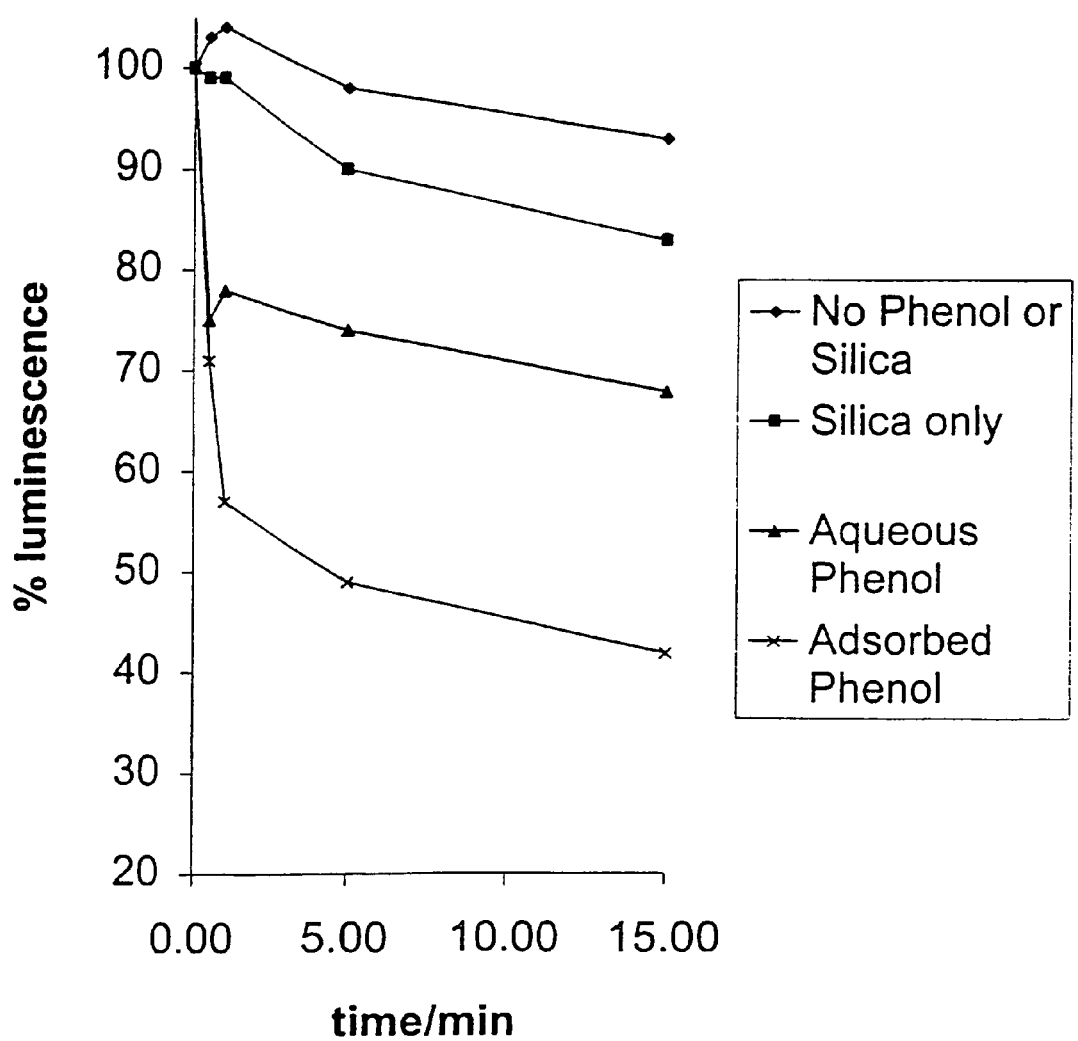
FIG. 1 is a graphic representation of the effect on % bioluminescence due to aqueous phenol and adsorbed phenol.

The Microtox® system described above utilizes the phenomenon of bioluminescence occurring in *Vibrio fischeri* bacteria, and such *Vibrio fischeri* bacteria are the preferred organisms used in the present invention. However, and as would be appreciated by those of skill in the art, it is possible to provide recombinant organisms, such as *E. coli*, which contain exogenous nucleic acids capable of conferring the bioluminescence phenotype on recombinant cells. Such nucleic acids will generally encode the enzyme luciferase cloned from naturally occurring bioluminescent organism for subsequent transformation of the microorganism of interest. A process for producing genetically modified bioluminescent microorganisms expressing the lux genes from Vibrio harveyi is described in U.S. Pat. No. 4,581,335.

In accordance with an alternative aspect of the invention, eukaryotic cells are used which have been transformed or transfected with a vector containing nucleic acid encoding a eukaryotic luciferase enzyme (luc) such as, for example, luciferase from the firefly Photinus Pyralis. A suitable plasmid vector containing cDNA encoding firefly luciferase under the control of an SV40 viral promoter is available from Promega Corporation, Madison, Wis., U.S.A. However, it is considered advantageous to use recombinant cells containing the entire eukaryotic luc operon so as to avoid the need to add an exogenous substrate (e.g. luciferin) in order to generate light output. The presence of a toxic substance or analyte in a sample has been shown to cause a reduction in light emission by such cells.

The analytes to be tested using the assay of the invention are usually toxic substances; however, the precise nature of the analyte to be tested is not material to the invention. Many toxicants and toxins are known to have the effect of reducing bioluminescence or some other signal-generating aspect of living cells.

Toxicity is a general term used to describe an adverse effect on a biological system, and the term toxic substances is intended to include both toxicants (chemicals that are toxic) and toxins (natural poisons). Toxicity is usually expressed as an effective concentration (EC) or an inhibitory concentration (IC) value. The EC/IC value is usually denoted as a percentage response e.g. $EC_{50}$, $EC_{10}$ which denotes the concentration (dose) of a particular substance which affects the designated criteria for assessing toxicity (i.e. a behavioral trait or death) in the indicated proportion of the microorganism population tested. For example, an $EC_{50}$ of 10 ppm indicates that 50% of the population will be affected by a concentration of 10 ppm. In the case of a toxicity assay based on the use of a bioluminescent assay reagent, the $EC_{50}$ value is usually the concentration of sample substance causing a 50% change in light output.

Materials and Methods

Two commercially available chromatography-grade silica gels, a chromatography grade alumina, and three polymeric sorbents (XAD resins which are Amberlite® resins sold worldwide by Rohm & Haas as polymeric adsorbents for the recovery of phenol and/or other organic substances) were evaluated, by testing their ability to adsorb malathion from aqueous solution. Malathion is a representative organophosphate which has been used effectively as an insecticide. The results are given in Table 1 which follows and show the capability of these adsorbents to sequester malathion from an aqueous solution containing 20 ppm.

TABLE 1

Malathion extraction by solid-phase adsorbents

| Material Tested | Amount of Malathion extracted/ppm | Amount of Malathion extracted % |
|---|---|---|
| XAD-4 | 19.6 | 97.8 |
| XAD-7 | 19.9 | 99.8 |
| XAD-16 | 19.9 | 99.6 |
| $Al_2O_3$ | 19.9 | 99.9 |
| Silica Gel (100–200 mesh) | 20 | 100 |
| Silica Gel (15–40 μm) | 19.9 | 99.9 |

It is apparent that malathion has an affinity for all of the adsorbents. Any or all of these adsorbents are considered to be potentially useful in methods and kits for practicing the invention, as well as cellulose and similar adsorbents. However, due its reported low toxicity towards the Microtox® microorganism, Vibrio fischeri, (Vaughan, 1995), it was decided to focus efforts upon utilizing silica as an adsorbent. Particulate silica is preferably used in the form of silica gel, an amorphous silica which is widely commercially available in a variety of size ranges. Very generally, particulate adsorbents of about 500 μm or less are preferred, with particles of 200 μm or less being more preferred; however, silica particles of about 100 μm or less are still more preferred, with silica particles of about 50 μm or below being most preferred.

Experiments were then performed to see if simple immobilization of Vibrio fischeri could be accomplished by using silica gel. Such immobilization was performed, and the resultant "paste" was used in test procedures to determine if such adsorption would enhance the subsequent response towards toxic chemicals.

The Microtox® Test

Briefly the Microtox® tests used for this study first involve rehydration of freeze-dried luminescent Vibrio fischeri bacteria, i.e. the Microtox® reagent.

The reconstituted bacterial suspension is added to a series dilution of sample in 2% NaCl and incubated for 15° C. for 0.5–15 minutes. The dilutions can be modified to give any desired concentration of sample, and the volume of reagent used per test can also be varied.

After incubation, bioluminescence is measured in a suitable photometer, such as a Deltatox® photometer or that in the Microtox® Model 500 Analyzer.

Data is recorded in terms of decrease luminescence over time.

Experiments are performed to examine the toxic effects from either malathion or phenol, which are representative of organic toxicants. Generally, these tests are carried out in the presence of an adsorbent which is referred to as using a modified Microtox® test.

In one embodiment of the invention, the solid-phase adsorbent is added to samples of toxicants and left for 30 minutes at ambient temperature. The amount of solid adsorbent and the concentrations of toxicant used are varied.

During this time, rehydration of the freeze-dried Microtox® bacteria as an aqueous suspension is performed, and it is left to stabilize at 15° C. for 15 minutes.

After the 30-minute period, the solid adsorbent, which now carries the adsorbed toxicant, is separated from the sample and added to the aqueous bacterial suspension and incubated.

At the same time, a control sample of bacteria is monitored for comparison. In addition, test using bacteria and silica alone and toxicant alone are performed.

After 30 minutes of incubation, the bioluminescence is measured using a photometer, and data is recorded in terms of decrease of luminescence over time.

Figure 2:
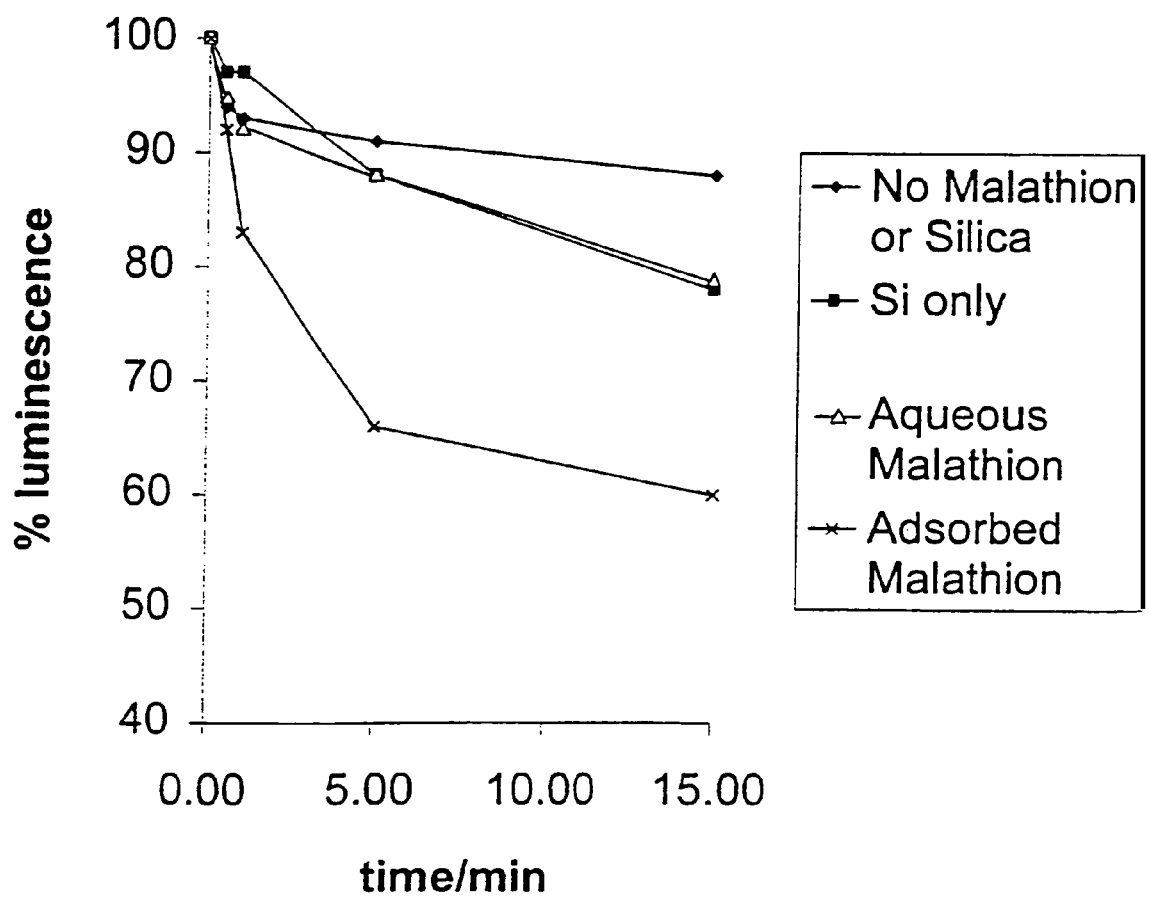
FIG. 2 is a graphic representation of the effect on % bioluminescence due to aqueous and adsorbed malathion.

The results of such experiments are described below in FIGS. 1 and 2. FIGS. 1 and 2 show the effect on the percent luminescence of *V. fischeri* when exposed to silica gel alone, aqueous phase toxicant and an adsorbed toxicant. It is apparent from these test results not only that a response can still be initiated from the microorganism when chemicals are adsorbed at a solid surface, but that the effect of a solid matrix enhances the response to the toxicant. After observing these experimental results, it was investigated whether a similar response would be elicited when bacteria or some equivalent biological reporter system were adsorbed onto a solid surface.

Results

For initial testing of such a bacteria/silica mixture, rehydration of freeze-dried luminescent *Vibrio fischeri* Microtox® reagent is carried out as before, and 4 aliquots are taken. One aliquot of the resultant suspension is mixed with 0.5 g of silica gel, although the amount of silica gel can be varied. After the bacteria are adsorbed onto the silica gel, the resultant mixture is used as the bioluminescent reagent in toxicity assays. Two of the other aliquots are used as controls (with and without silica gel), and the third is tested with toxicant alone.

The first aliquot of reconstituted bacterial suspension is added to a series dilution of toxic sample in 2% NaCl and incubated at 15° C. for 0.5–15 minutes as is one other aliquot with silica gel. The dilutions can be modified to give any desired concentration of toxic sample, but the amount of reagent used per test is kept constant.

After incubation, bioluminescence is measured using a photometer, and data is recorded in terms of decrease of luminescence over time.

Figure 3:
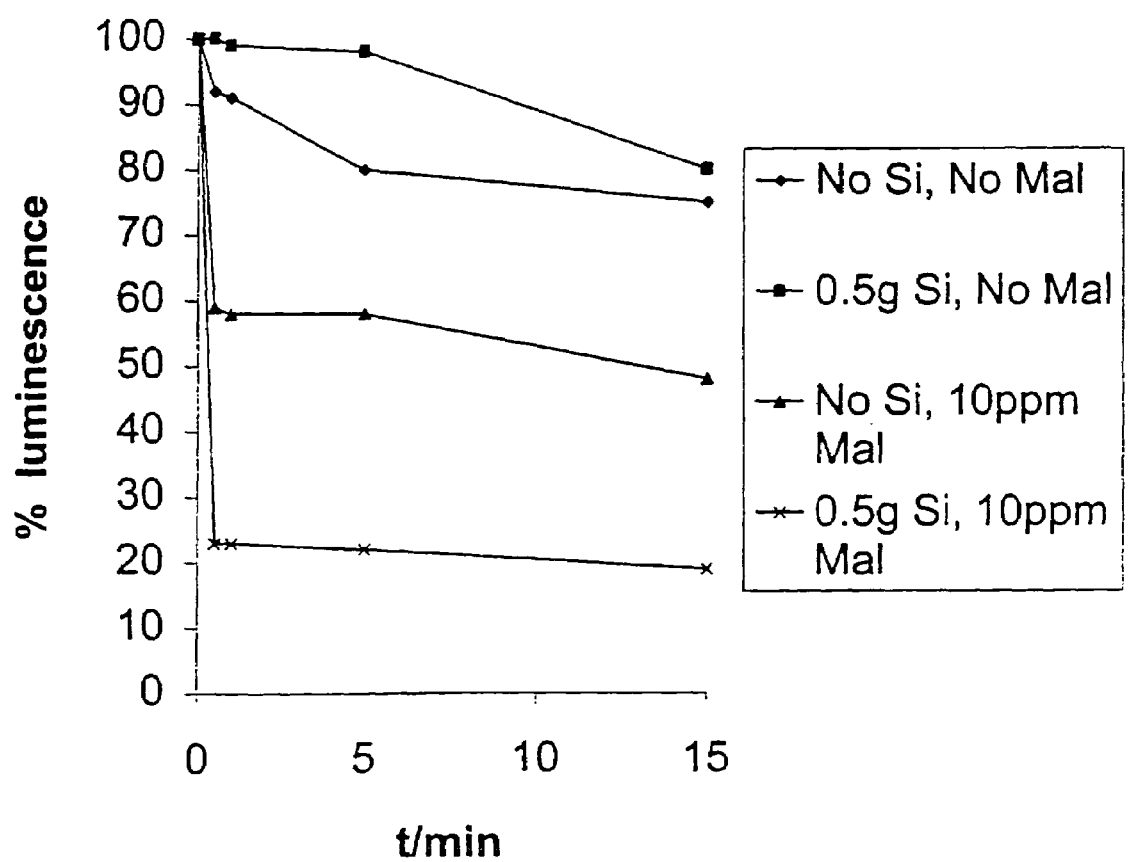
FIG. 3 is a graphic representation of the effect of malathion on % bioluminescence exhibited by "free" and immobilized bacteria.
Figure 4:
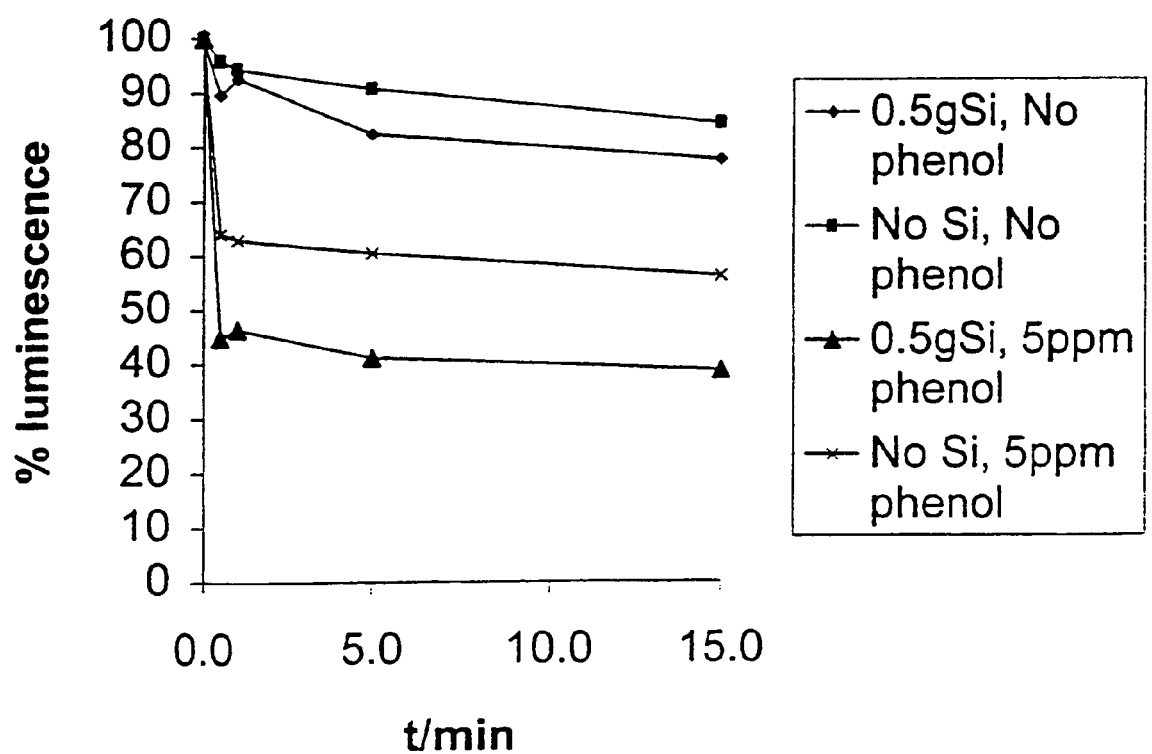
FIG. 4 is a graphic representation of the effect of phenol on % bioluminescence exhibited by "free" and immobilized bacteria.

FIGS. 3 and 4 show the effect of using the bacteria/silica mixture. It is clear that the effect is to enhance the response of *Vibrio fischeri*, i.e. decreased luminescence, compared to the normal reagent alone in the presence of a like concentration of toxicant. The tests show that the bacteria adsorbed upon silica surfaces result in an enhanced response when exposed to toxic chemicals. This observation is unexpected, as at present no other enhancement effect such as this is believed to have been reported in the literature.

Estimates of the number of free *Vibrio fischeri* in solution before and after contact with silica indicate that the presence of silica reduces the number of free bacteria by a factor of 100. This factor may be important in that bacterial numbers could influence the interaction and subsequent bioavailability of toxicant compounds.

Stabilization of the bacteria used in the standard Microtox® test is performed by freeze-drying, and the effects of stabilization on such a bacteria-silica mixture were also investigated. A bacteria-silica mixture at a specific bacteria to silica ratio is subjected to freeze-drying at −30° C. for 6 hours under a vacuum, i.e. 0.1 hPa. Thereafter, the temperature is ramped up to +15° C. at increments of 10° C. per 15 minutes, retaining the vacuum, and then held at +15° C. for 8 hours.

Figure 5:
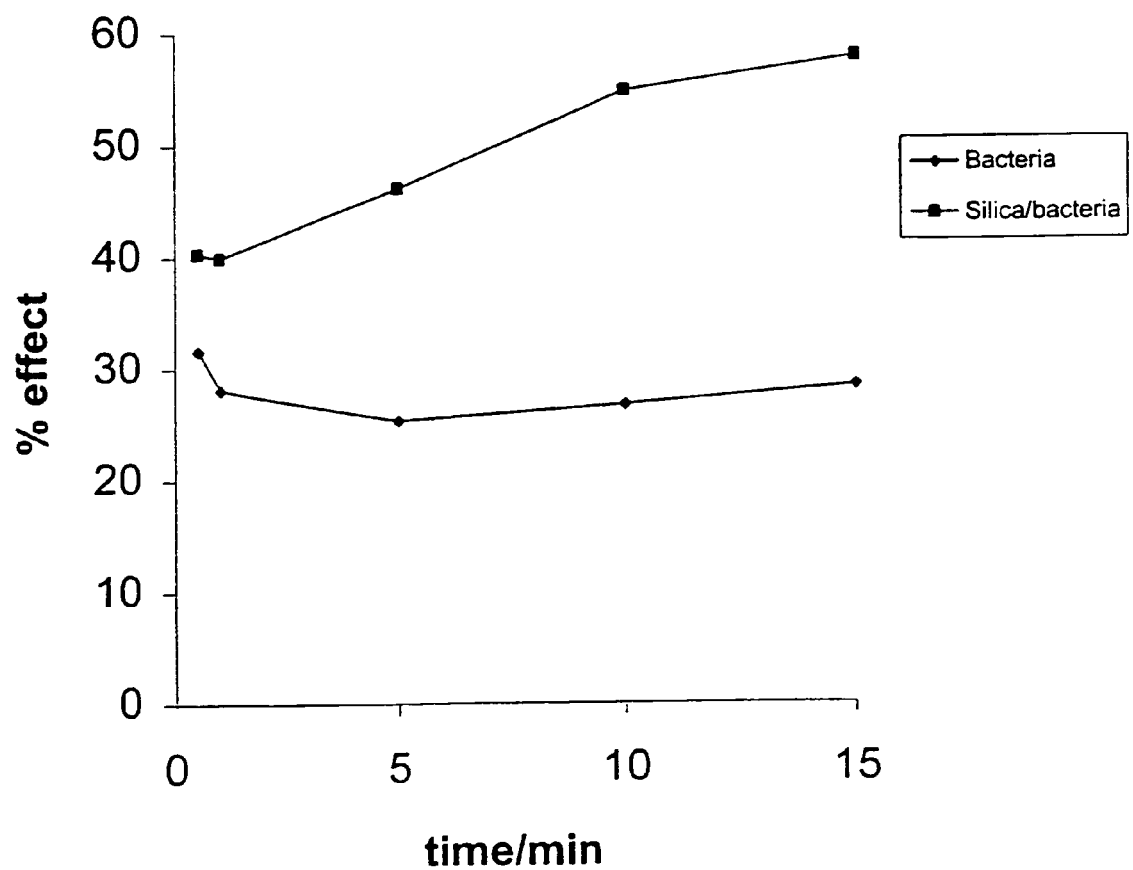
FIG. 5 is a graphic representation of the mean % effect for a toxicity assay with 10 ppm malathion upon stabilized (freeze dried) silica-based cellular reagent and "free" cellular reagent.

Tests are then run to compare this freeze-dried mixture with the standard Microtox® freeze-dried reagent. FIG. 5 shows the data for a toxicity assay with 10 ppm of malathion using reagents which provide comparable concentrations of standard freeze-dried Microtox® bacteria and a stabilized silica-based reagent mixture which was subjected to freeze-drying under the conditions indicated above. FIG. 5 shows that, compared to its effect upon the standard Microtox® reagent, the toxic effect of malathion is increased, the % toxic effect being reported is the difference between the natural decrease of bioluminescence in a control sample of freeze-dried bacteria in comparison to the greater decrease in bioluminescence in comparable samples when exposed to a selected concentration of a toxicant.

Toxicity is a general term used to describe an adverse effect on a biological system. By definition toxicity can only be measured by a biological system; thus, specific chemical estimates of a toxicant cannot be related to the toxic effect of the chemical. The test results (FIGS. 1 and 2) show that the toxicity effect of both phenol and malathion is increased when the toxicant is adsorbed onto a solid surface, such relative toxicity being measured as the effect on luminescence and compared to aqueous suspensions of bacteria with and without toxicant.

It is considered important that this study shows that the toxic effect of an aqueous concentration of phenol or malathion upon such a bioluminescent system can be enhanced by immobilizing bacteria (*V. fischeri*) by adsorption onto a solid surface (see FIGS. 3, 4 & 5), thus creating an expedient, more sensitive assay. This effect could be a consequence of a combination of influences upon bacterial numbers, effects of bioavailability due to immobilization, and partitioning of the chemicals to solid surfaces, with the last point resulting in a steeper concentration gradient of the toxicant and subsequent faster mass transfer due to shorter diffusion distances.

Although the invention has been described with regard to certain preferred embodiments which constitute the best mode presently known to the inventors, it should be understood that various changes and modifications as may be obvious to those having ordinary skill in this art may be made without departing from the scope of the invention which is set forth in the claims appended hereto. For example, kits for carrying out such assays might have a plurality of cuvettes or like containers for contacting the analyte and the reagent in an aqueous medium, along with reagent, reconstitution buffer, pipette syringes, pipette tips and the like. Particular features of the invention are accentuated in the claims that follow.

The invention claimed is:

1. A method of detecting a potentially toxic analyte comprising:
    (a) measuring a signal generated by preparing a test suspension comprising the potentially toxic analyte to be detected with a cellular reagent in the form of a preparation of eukaryotic or prokaryotic cells having signal-generating metabolic activity, wherein said cellular reagent is adsorbed onto a particulate solid-phase carrier having a particle size of 500 µm or less;
    (b) measuring a control signal generated by preparing a control suspension comprising the cellular reagent without the potentially toxic analyte; and
    (c) comparing the signals generated in (a) and (b), wherein a decrease in the signal in (a) as compared to (b) indicates detection of the toxic analyte.

2. The method of claim 1, wherein said cellular reagent is subjected to a stabilization step prior to being used in said method.

3. The method of claim 2, wherein said stabilization step comprises freeze-drying a mixture of said cellular reagent and a particulate carrier.

4. The method of claim 1 wherein said signal-generating metabolic activity is bioluminescence and the particulate solid-phase carrier is inorganic.

5. The method of claim 4 wherein said preparation of prokaryotic or eukaryotic cells are cells which have been genetically modified to exhibit bioluminescence.

6. The method of claim 5 wherein said cells have been genetically modified to contain a nucleic acid encoding luciferase.

7. The method of claim 1 wherein said preparation of prokaryotic cells are bacteria.

8. The method of claim 7 wherein said bacteria are *Vibrio fischeri*.

9. The method of claim 1 wherein the particulate solid phase carrier is particulate silica.

10. The method of claim 1, wherein the particulate solid phase carrier comprises an organic or inorganic particulate.

11. The method of claim 1 wherein the particulate solid phase carrier is selected from the group consisting of polymers, alumina and cellulose.

12. A method of preparing to assay a potentially toxic analyte, said method comprising immobilizing or adsorbing onto a particulate solid-phase carrier a preparation of eukaryotic or prokaryotic cells having signal-generating metabolic activity wherein the solid-phase carrier has a particle size of 500 µm or less.

13. The method of claim 12, wherein the eukaryotic or prokaryotic cells having signal-generating metabolic activity are subjected to a stabilization step prior to being used in the method.

14. The method of claim 13, wherein the stabilization step comprises freeze-drying a mixture of the eukaryotic or prokaryotic cells having signal-generating metabolic activity and the particulate carrier.

* * * * *